(12) United States Patent
Lin

(10) Patent No.: US 11,229,243 B2
(45) Date of Patent: Jan. 25, 2022

(54) THERAPEUTIC BRA STRUCTURE

(71) Applicant: I MOSA Corp., Taipei (TW)

(72) Inventor: Yen-Ting Lin, New Taipei (TW)

(73) Assignee: I MOSA CORP., Taipei (TW)

( * ) Notice: Subject to any disclaimer, the term of this patent is extended or adjusted under 35 U.S.C. 154(b) by 334 days.

(21) Appl. No.: 16/407,973

(22) Filed: May 9, 2019

(65) Prior Publication Data

US 2019/0364980 A1 Dec. 5, 2019

(30) Foreign Application Priority Data

Jun. 1, 2018 (TW) .................................. 107207323

(51) Int. Cl.
| | | |
|---|---|---|
| *A41C 3/00* | (2006.01) | |
| *A61F 2/52* | (2006.01) | |
| *A61M 1/02* | (2006.01) | |
| *A61M 27/00* | (2006.01) | |
| *A61F 2/78* | (2006.01) | |

(52) U.S. Cl.
CPC .......... *A41C 3/0064* (2013.01); *A41C 3/0028* (2013.01); *A61F 2/52* (2013.01); *A61M 1/02* (2013.01); *A61M 27/00* (2013.01); *A61F 2002/7862* (2013.01); *A61M 2209/088* (2013.01)

(58) Field of Classification Search
CPC .................. A41C 3/0054; A41C 3/0028; A61F 2002/7862; A61F 2/52; A61M 2209/088; A61M 2210/1007

USPC .......................................................... 450/58
See application file for complete search history.

(56) References Cited

U.S. PATENT DOCUMENTS

| | | | | |
|---|---|---|---|---|
| 4,217,905 A | * | 8/1980 | Atwater ............... | A41C 3/0057 450/74 |
| 4,325,378 A | * | 4/1982 | Wilkinson ............... | A41C 3/02 450/58 |
| 5,158,541 A | * | 10/1992 | McCurley ............. | A61F 13/145 450/55 |
| 5,257,956 A | * | 11/1993 | Ewen ..................... | A41C 3/148 2/102 |
| 5,427,563 A | * | 6/1995 | Manning ................... | A61F 7/02 2/73 |
| 5,429,593 A | * | 7/1995 | Matory ................ | A61F 13/145 2/114 |

(Continued)

*Primary Examiner* — Gloria M Hale
(74) *Attorney, Agent, or Firm* — Muncy, Geissler, Olds and Lowe, P.C.

(57) ABSTRACT

A therapeutic bra structure includes a bra body having a bra layered member and a side bra layered member on both sides of the bra layered member separately, a fastener assembly or adhesive assembly combined with a distal edge of the side bra layered member and an elastic adjusting assembly having two elastic adjusting layers. Each elastic adjusting layer has an elastic and permeable layered member, and the two elastic adjusting layers are fixed to an inner side of the bra layered member, and an end adhesive assembly is provided at an outer edge of the elastic adjusting layers for the purpose of combining and positioning. This structure allows users to adjust the elasticity and has the effects of healing the wound stably, facilitating the use and installation of a drainage tube or an artificial blood vessel, and ensuring the safety of wearing bra after breast surgery.

14 Claims, 11 Drawing Sheets

(56) References Cited

U.S. PATENT DOCUMENTS

| | | | | |
|---|---|---|---|---|
| 5,950,238 | A * | 9/1999 | Klein | A41D 13/1245 2/69 |
| 5,956,764 | A * | 9/1999 | Sabin | A41D 13/00 2/69 |
| 5,960,474 | A * | 10/1999 | Dicker | A42B 3/0406 2/69 |
| 5,968,003 | A * | 10/1999 | Sisson | A41C 3/0064 602/19 |
| 6,048,252 | A * | 4/2000 | Sebring | A41C 3/148 450/1 |
| 6,755,717 | B2 * | 6/2004 | Smith | A41C 3/0057 128/869 |
| 7,396,272 | B1 * | 7/2008 | Newlen | A41D 13/1245 2/114 |
| 7,909,675 | B1 * | 3/2011 | Rainey | A41C 3/148 450/59 |
| 8,100,848 | B2 | 1/2012 | Wilkes et al. | |
| 8,696,403 | B2 * | 4/2014 | Haley | A41C 3/0028 450/36 |
| 8,926,398 | B1 * | 1/2015 | Mendeleev | A41C 3/08 450/61 |
| 9,756,880 | B1 * | 9/2017 | Malik | A41C 3/12 |
| 10,136,681 | B1 * | 11/2018 | Malik | A41C 3/0035 |
| 10,986,880 | B2 * | 4/2021 | Stephens | A41C 3/12 |
| 2009/0158491 | A1 * | 6/2009 | Maier | A41D 13/02 2/78.1 |
| 2013/0084776 | A1 * | 4/2013 | Walsh | A41C 3/12 450/57 |
| 2015/0264982 | A1 * | 9/2015 | Randall | A41C 3/0057 450/52 |
| 2015/0296896 | A1 * | 10/2015 | Laguna | A61F 13/14 450/58 |
| 2015/0366281 | A1 * | 12/2015 | Miller | B32B 5/26 428/136 |
| 2016/0278461 | A1 * | 9/2016 | Corrado | A41C 3/0064 |
| 2017/0135847 | A1 * | 5/2017 | Leibowitz | A41C 3/04 |
| 2017/0143049 | A1 * | 5/2017 | Oguchi | A41C 3/144 |
| 2017/0202274 | A1 * | 7/2017 | Blackwell | A41C 3/02 |
| 2018/0084845 | A1 * | 3/2018 | Cumiskey | A41D 27/10 |
| 2019/0029334 | A1 * | 1/2019 | Wolff | A41C 3/0078 |
| 2020/0077718 | A1 * | 3/2020 | Thompson | A41D 13/1281 |
| 2021/0145098 | A1 * | 5/2021 | Mabon | A41C 3/00 |

* cited by examiner

THERAPEUTIC BRA STRUCTURE

FIELD OF THE INVENTION

The present invention relates to a bra structure, and more particularly to a therapeutic bra structure to be used during a female breast surgery healing period or a repair and modification period after healing.

BACKGROUND OF THE INVENTION

Due to the stressful working pattern and complicated lifestyle nowadays, people have serious illnesses. For example, women's top ten diseases include breast cancer, colorectal cancer, lung cancer, liver cancer, thyroid cancer, endometrial cancer, cervical cancer, skin cancer, ovarian cancer, and gastric cancer. As medicine advances, many diseases can be treated by appropriate drug selection and early examination and surgery. Of course, a proper handling in the whole healing period is also very important. For example, female patients have to consider wearing a therapeutic bra for healing and repairing after a breast cancer surgery.

After a female breast surgical operation, the wound is wrapped by thick gauze or yarn and pressed by a corset (if necessary) to avoid breeding too much or cracking the wound. After the wound is pressed by the corset, blood stasis may occur at the wound, and the corset may also have the effects of squeezing or removing the blood stasis appropriately. Obviously, it is necessary to handle the blood stasis and leakage properly to avoid re-contaminating the wound or prevent blood from penetrating through and staining the corset that creates a visual psychological burden. Since it is necessary to closely observe whether or not blood comes out from the breast wound during the healing period or whether or not the surrounding of the wound is swollen, therefore one or two drainage tubes are placed at the breast wound to drain blood or an artificial blood vessel is installed and provided for blood transfusion. Attention should be paid to the acute pulmonary embolism which is a "post-surgery fatal killer", and the situation of having insufficient blood to be delivered to the lungs for oxygen exchange may lead to possible acute respiratory failure, fainting, shock, or even sudden death.

Therefore, women have to pay close attention to the protection of the wound during the healing period after a breast surgery. For example, moving the gauze/yarn may affect wound healing. In addition, the installation of drainage tubes or artificial blood vessels may even improve the cleaning and repairing effects during the healing period. However, a conventional bra assembly does not have these functions. Therefore, it is an important subject for related manufacturers to overcome the aforementioned drawbacks and provide an appropriate bra to women during the healing period and repairing period after a breast surgery.

In view of the drawbacks with regard to the use of the conventional bra structure during the surgery healing period/repairing period and the poor structural design, the inventor of the present invention based on years of experience in the related industry to conduct extensive research and experiment, and finally developed and provided a therapeutic bra structure with better adjustability, convenience, and safety to serve the general public and promote the development of this industry.

SUMMARY OF THE INVENTION

It is a primary objective of the present invention to overcome the aforementioned drawbacks of the prior art by providing a therapeutic bra structure with the effects of facilitating its use for women during a breast surgery healing period, adjusting the elasticity of the bra structure appropriately to ensure that the wound can be healed stably and to facilitate the installation and use of a drainage tube or an artificial blood vessel, and ensuring the wearing safety the bra after surgery.

Another objective of the present invention is to provide a therapeutic bra structure for the use by women after a breast surgery healing period and during a repair and modification period, so that the patient can recover her normal life quickly and prevent further psychological harm.

A further objective of the present invention is to provide a therapeutic bra structure capable of removing some blood stasis and stopping blood leakage after the wound is pressed and wrapped appropriately, so that the blood stasis can be absorbed and the blood leakage can be handled properly to avoid re-contaminating the wound or prevent blood from penetrating through and staining the corset that creates a visual psychological burden.

To achieve the aforementioned and other objectives, the present invention provides a therapeutic bra structure comprising: a bra body, having a bra layered member, with a side bra layered member disposed on both sides of the bra layered members separately, and a fastener assembly or an adhesive assembly combined with an edge of the two side bra layered members; an elastic adjusting assembly, having two elastic adjusting layers, each having an elastic and permeable layered member, and the two elastic adjusting layers being combined and fixed to an inner side of the bra layered member and having an end adhesive assembly disposed on an outer side of the two elastic adjusting layers separately and provided for a purpose of combining and positioning.

In this embodiment, the bra layered member, the bra layered member has two corresponding longitudinal strip shaped adhesive assemblies, and the elastic adjusting layer has a longitudinal strip shaped adhesive assembly disposed on an outer side of an inner edge of the elastic adjusting layer.

In this embodiment, the bra layered member has two corresponding lump adhesive assemblies, and the elastic adjusting layer has a lump adhesive assembly disposed on an outer side of an upper edge of the elastic adjusting layer.

In this embodiment, the bra layered member has two shoulder straps disposed thereon, and the shoulder strap has an adjusting fastener.

In this embodiment, the bra layered member has two corresponding pockets, and each of the two pockets has an accommodating opening.

In this embodiment, the bra layered member has at least one positioning hole provided for passing, installing, and positioning a drainage tube or an artificial blood vessel.

This embodiment further comprises at least one breast prosthesis pad, and the breast prosthesis pad further comprises a breast prosthesis pad member and a breast prosthesis strap, and the breast prosthesis strap is put into the pocket through the accommodating opening for the purpose of positioning.

In this embodiment, the elastic adjusting layer further comprises an absorbing and positioning device, and the absorbing and positioning device comprises an outer positioning piece and a positioning lining combined with each other.

In this embodiment, a positioning strap space is formed between the outer positioning piece and the positioning lining, and an absorbing cotton strap is installed in the positioning strap space.

In this embodiment, the positioning strap space is a positioning pocket, and the positioning pocket has at least one opening formed on the positioning lining.

In this embodiment, the positioning lining is strip shaped, and both distal ends of the positioning lining are sewed and fixed to the outer positioning piece, and the positioning strap space is provided for passing, installing, and positioning the absorbing cotton strap.

In this embodiment, the outer positioning piece is provided for forming the end adhesive assembly thereon.

In this embodiment, the outer positioning piece is formed by the end adhesive assembly.

In this embodiment, the absorbing cotton strap covers the positioning lining.

DESCRIPTION OF THE PREFERRED EMBODIMENTS

The technical contents of the present invention will become apparent with the detailed description of preferred embodiments accompanied with the illustration of related drawings as follows. It is intended that the embodiments and figures disclosed herein are to be considered illustrative rather than restrictive.

Figure 1:
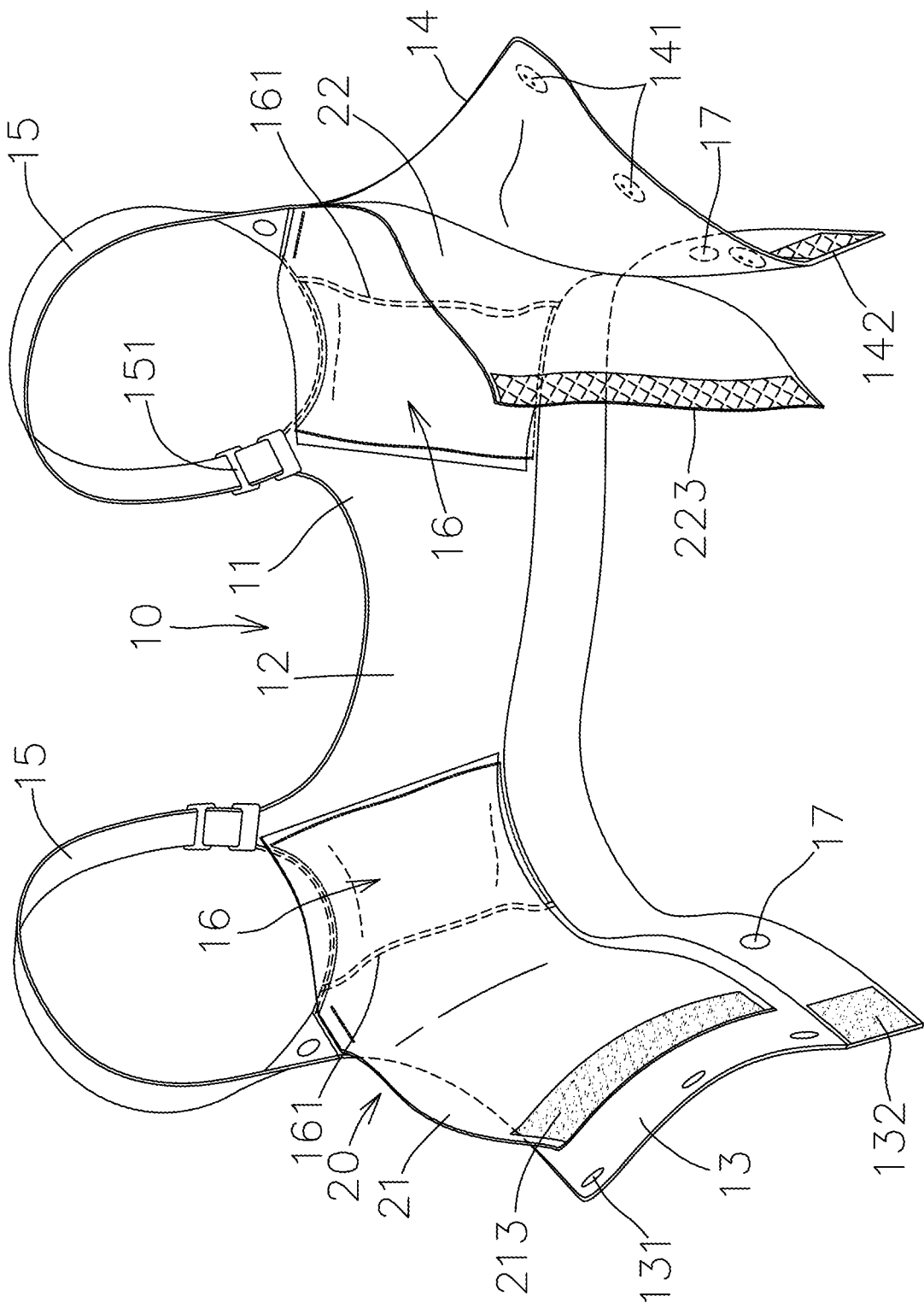
FIG. 1 is a perspective view of the present invention.
Figure 2:
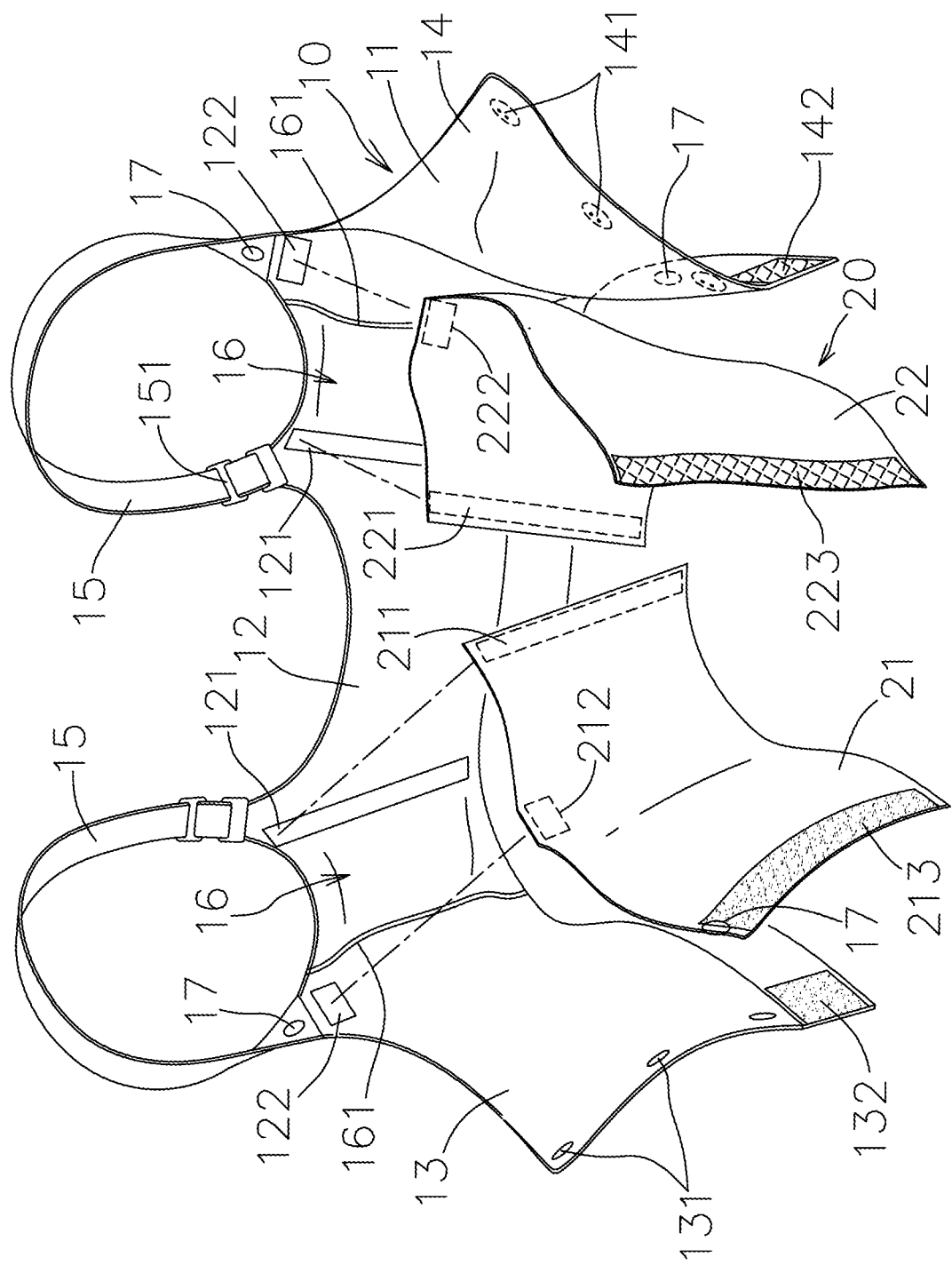
FIG. 2 is an exploded view of the present invention.

With reference to FIGS. 1 and 2 for a therapeutic bra structure of the present invention, the therapeutic bra structure comprises a bra body 10 and an elastic adjusting assembly 20, and the bra body 10 comprises a bra layered member 11, and the bra layered member 11 further comprises a central bra layered member 12 and two side bra layered members 13, 14 disposed on both sides of the central bra layered member 12 respectively. In other words, the central bra layered member 12 and two side bra layered members 13, 14 are combined to form the bra layered member 11. Wherein, the bra layered member 11 (including the central bra layered member 12) has two corresponding strip shaped adhesive assemblies 121, and the bra layered member 11 has two bumpy adhesive assemblies 122 disposed at an upper edge thereof, and a fastening hole 131 is formed at a distal edge of the side bra layered member 13, and a fastener 141 is disposed at a distal edge of the side bra layered member 14. Of course, the position of the fastening hole 131 and the position of the fastener 141 can be switched to form a fastener assembly, so that the fastening hole 131 and the fastener 141 can be engaged with each other. An adhesive assembly 132 is disposed on an inner side of a distal edge of the side bra layered member 13 (and at a position close to the user's body), and an adhesive assembly 142 is disposed on an outer side of a distal edge of the side bra layered member 14 (and at a position away from the user's body), and the adhesive assembly 132 and the adhesive assembly 142 are provided for adhering with each other. Of course, the positions of the adhesive assembly 132 and the adhesive assembly 142 can be switched.

In addition, the bra body 10 has two shoulder straps 15 disposed at the top of the bra layered member 11, and each shoulder strap 15 has an adjusting fastener 151. The bra body 10 has two corresponding pockets 16 formed at appropriate positions of the bra layered member 11 respectively and the two pockets 16 are substantially disposed at the junction of the central bra layered member 12 and the two side bra layered members 13, 14, but this invention is not limited to such arrangement only. The pocket 16 has an accommodating opening 161, and the bra layered member 11 has at least one positioning hole 17 formed at an appropriate position thereof. In the figure, the positioning hole 17 is formed at the upper edge or lower edge of the bra layered member 11, but this invention is not limited to these positions only. The positioning hole 17 is provided for passing, installing and positioning a drainage tube or a blood transfusion tubing.

The elastic adjusting assembly 20 comprises two elastic adjusting layers 21, 22, and the elastic adjusting layer 21, 22 has an elastic and permeable layered member, and the elastic adjusting layer 21, 22 has a longitudinal strip shaped adhesive assembly 211, 221 installed on an outer side of an inner distal edge thereof separately, and the elastic adjusting layer 21, 22 has a bumpy adhesive assembly 212, 222 disposed on an outer side of the upper edge thereof. The adhesive assembly 211, 221 is provided for adhering and engaging the two adhesive assemblies 121, and the adhesive assembly 212, 222 is provided for adhering and engaging the two adhesive assemblies 122, so as to fix the elastic adjusting layer 21, 22 (or the elastic adjusting assembly 20) onto the bra layered member 11 (which is the inner side position). The elastic adjusting layer 21 has an end adhesive assembly 213 disposed on an inner side of an outer distal edge thereof, and the elastic adjusting layer has an end adhesive assembly 223 22 disposed on an outer side of an outer distal edge thereof, and the end adhesive assemblies 213, 223 are adhered and engaged with each other. In addition, the elastic binding force of elastic adjusting layers 21, 22 can be adjusted by moving the adhering/engaging position.

Figure 3:
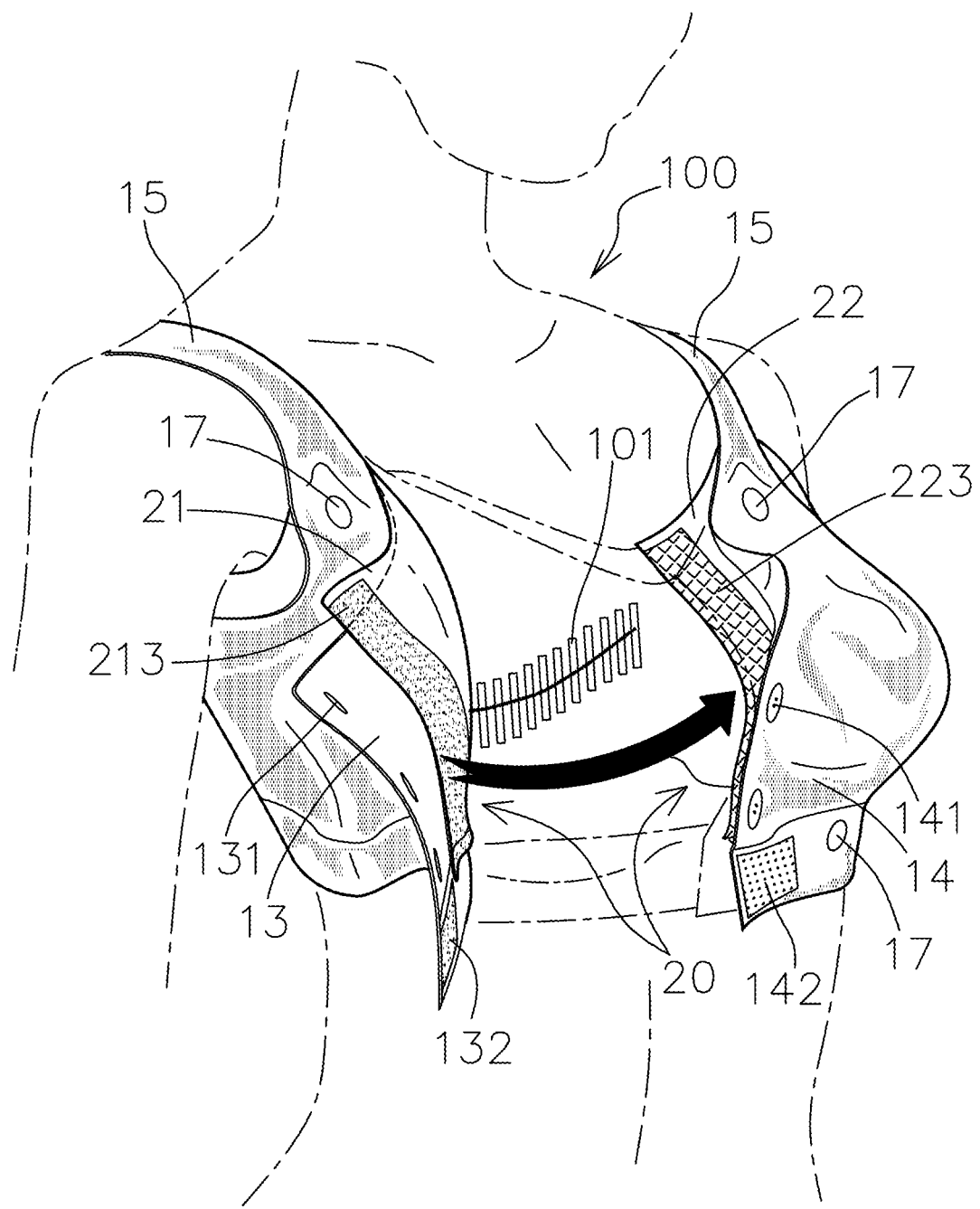
FIG. 3 is a schematic view of using the present invention during a healing period.

With reference to FIG. 3 for a using condition of a therapeutic bra structure during a healing period after surgery in accordance with the present invention, the elastic adjusting layer 21, 22 (or the elastic adjusting assembly 20) are fixed onto the bra layered member 11 first, and then the bra layered member 11 (or the bra body 10) is worn by a patient 100 by the shoulder strap 15, and the elasticity of the elastic adjusting layers 21, 22 is adjusted appropriately, so that the elastic adjusting layers 21, 22 can be attached onto the wound 101 securely to prevent the wound 101 from being hurt by the patient's physical movement or affecting the healing ability or causing a wound expansion. The fastener 141 and the fastening hole 131 are engaged with each other, and the positions of the adhesive assembly 132 and the adhesive assembly 142 can be adjusted for a better adhesion and engagement, so as to complete the wearing of the therapeutic bra structure and use the structure for fixing the wound in an appropriate positon during the healing period. In the meantime, the positioning hole 17 is provided for passing, installing and positioning a drainage tube or an artificial blood vessel to drain or transfuse blood, so as to ensure safe control during the healing period.

Figure 4:
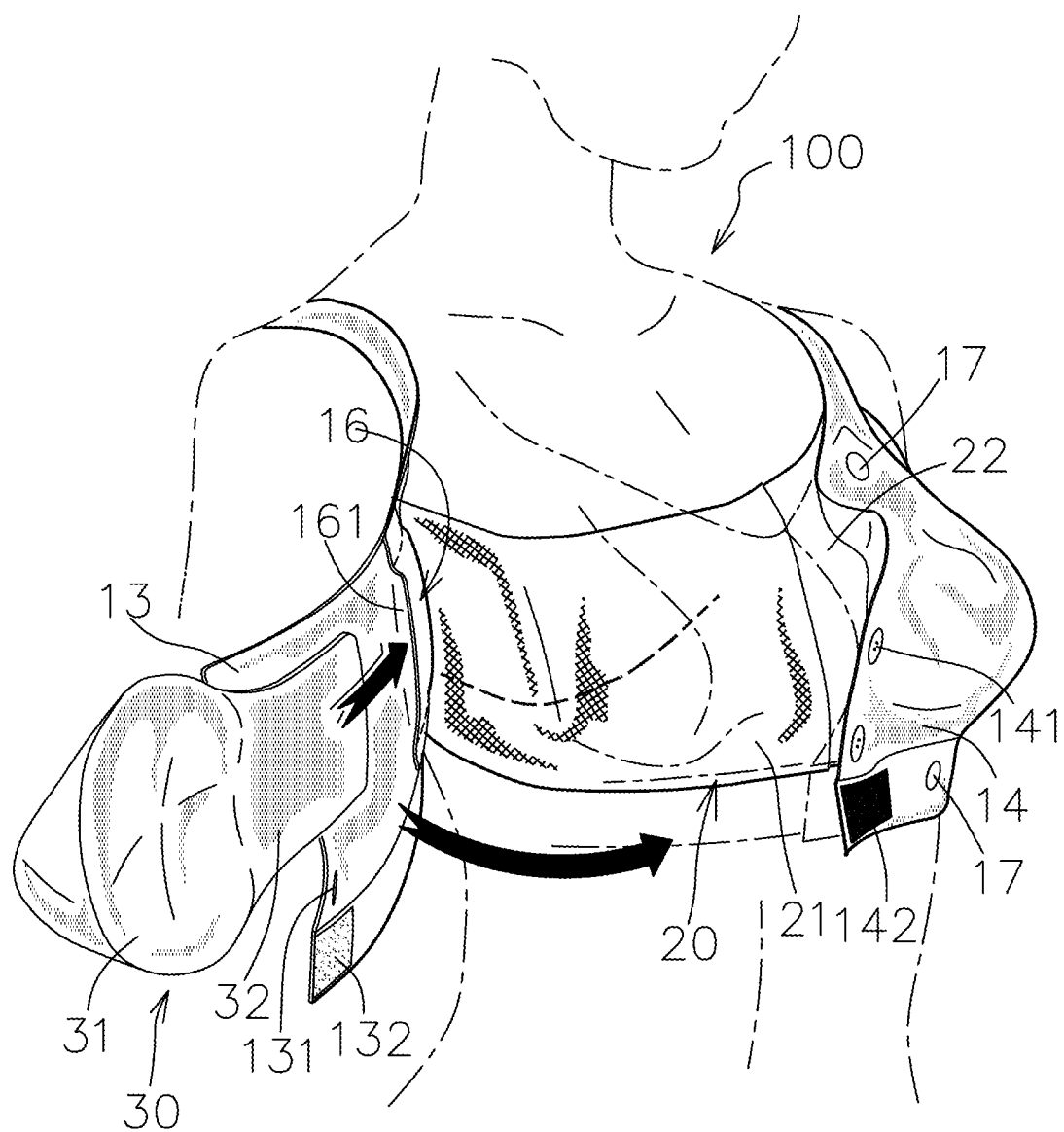
FIG. 4 is a schematic view of using the present invention during a repair and modification period after surgery healing.
Figure 5:
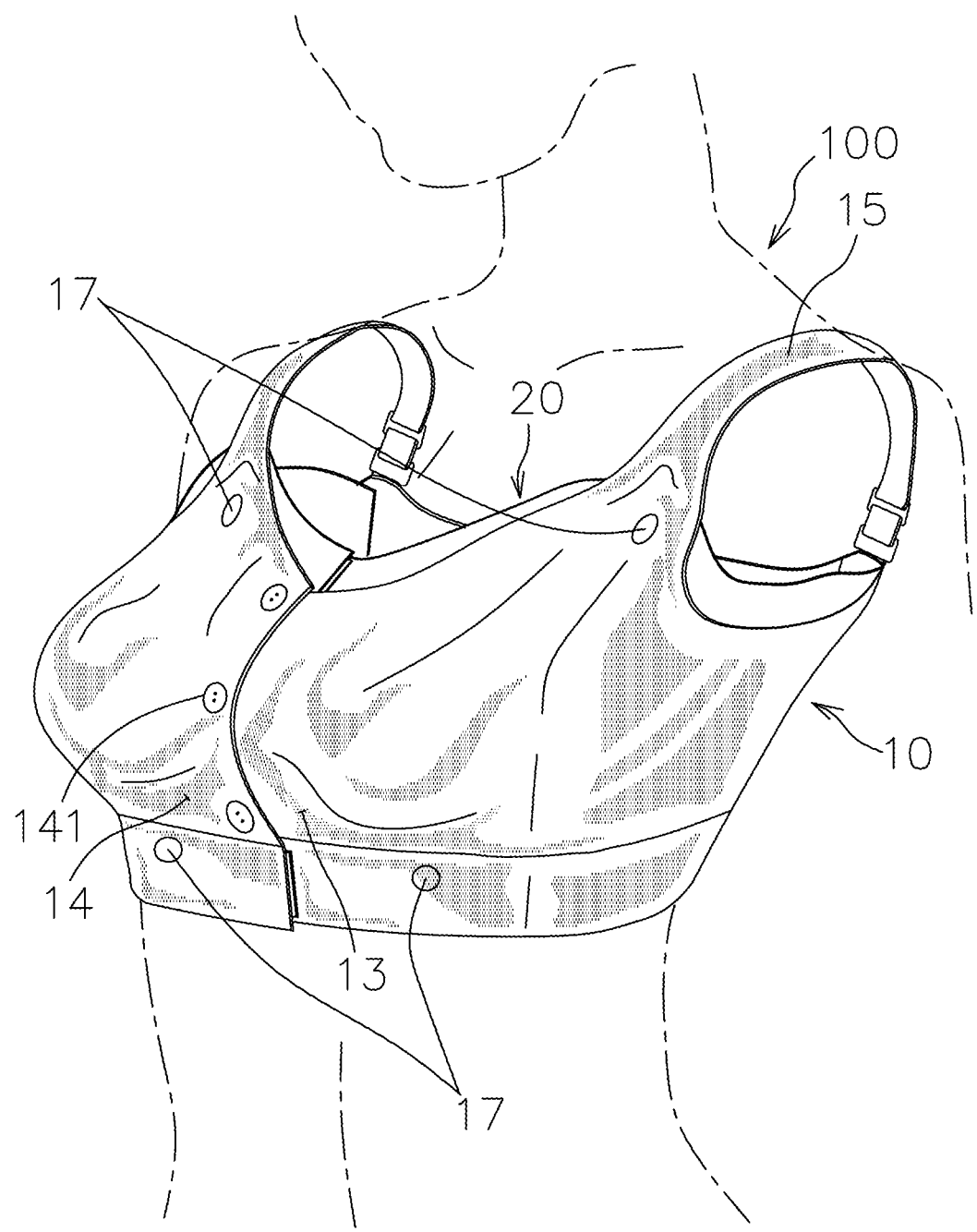
FIG. 5 is a schematic view of using the present invention during a repairing period after surgery healing.

With reference to FIG. 4 for the application of a therapeutic bra structure of the present invention during a repairing period after surgery healing, the present invention further comprises two breast prosthesis pads 30, and each breast prosthesis pad 30 comprises a breast prosthesis pad member 31 and a breast prosthesis strap 32. During use, the breast prosthesis strap 32 is placed into the pocket 16 from the accommodating opening 161 to get a better positioning effect, and then the elastic adjusting layers 21, 22 and the side bra layered members 13, 14 are positioned and engaged with each other to complete the installation, wearing, and use of the breast prosthesis pad 30 as shown in FIG. 5.

Figure 6:
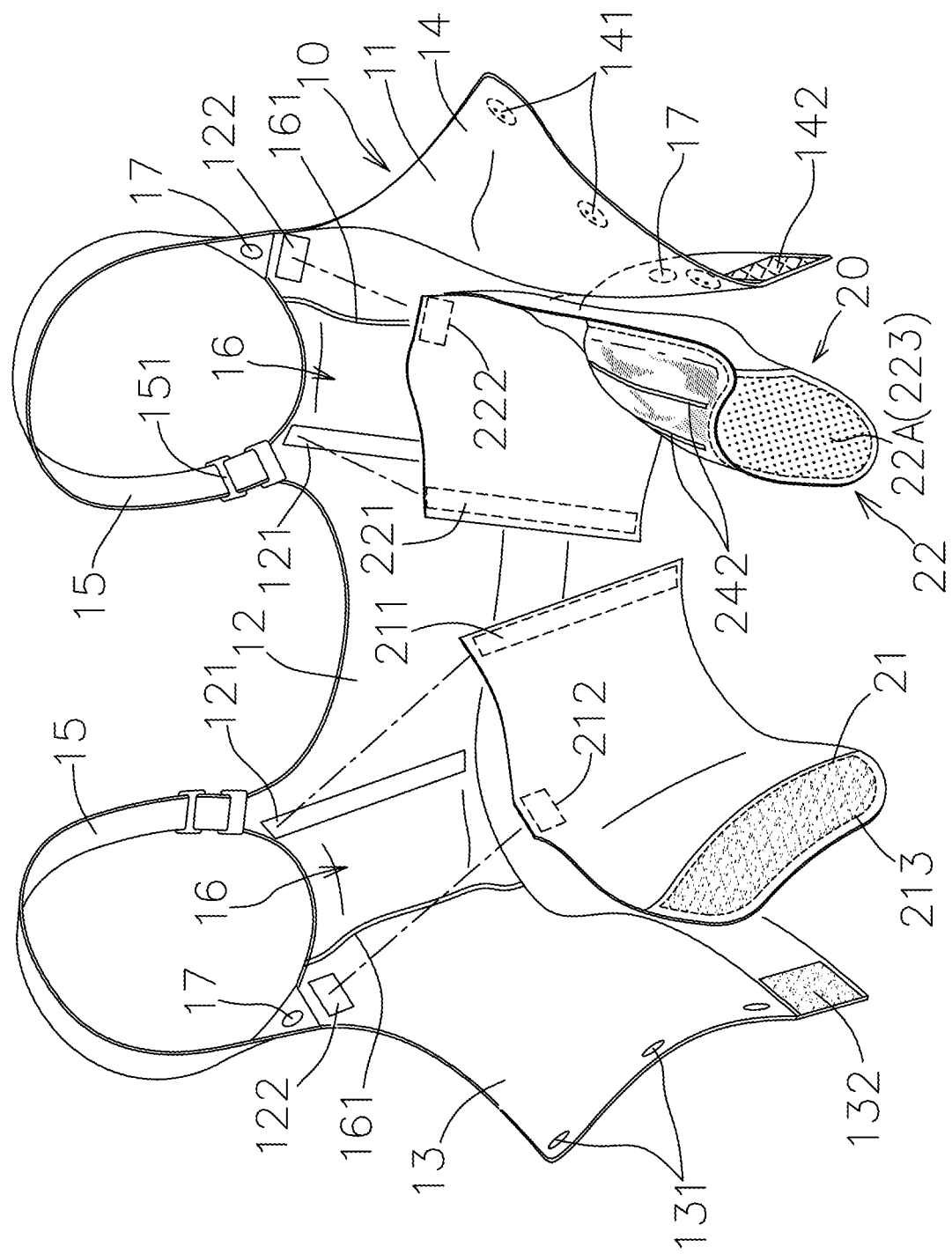
FIG. 6 is an exploded view of the present invention used during a healing period in accordance with an embodiment of the invention.
Figure 7:
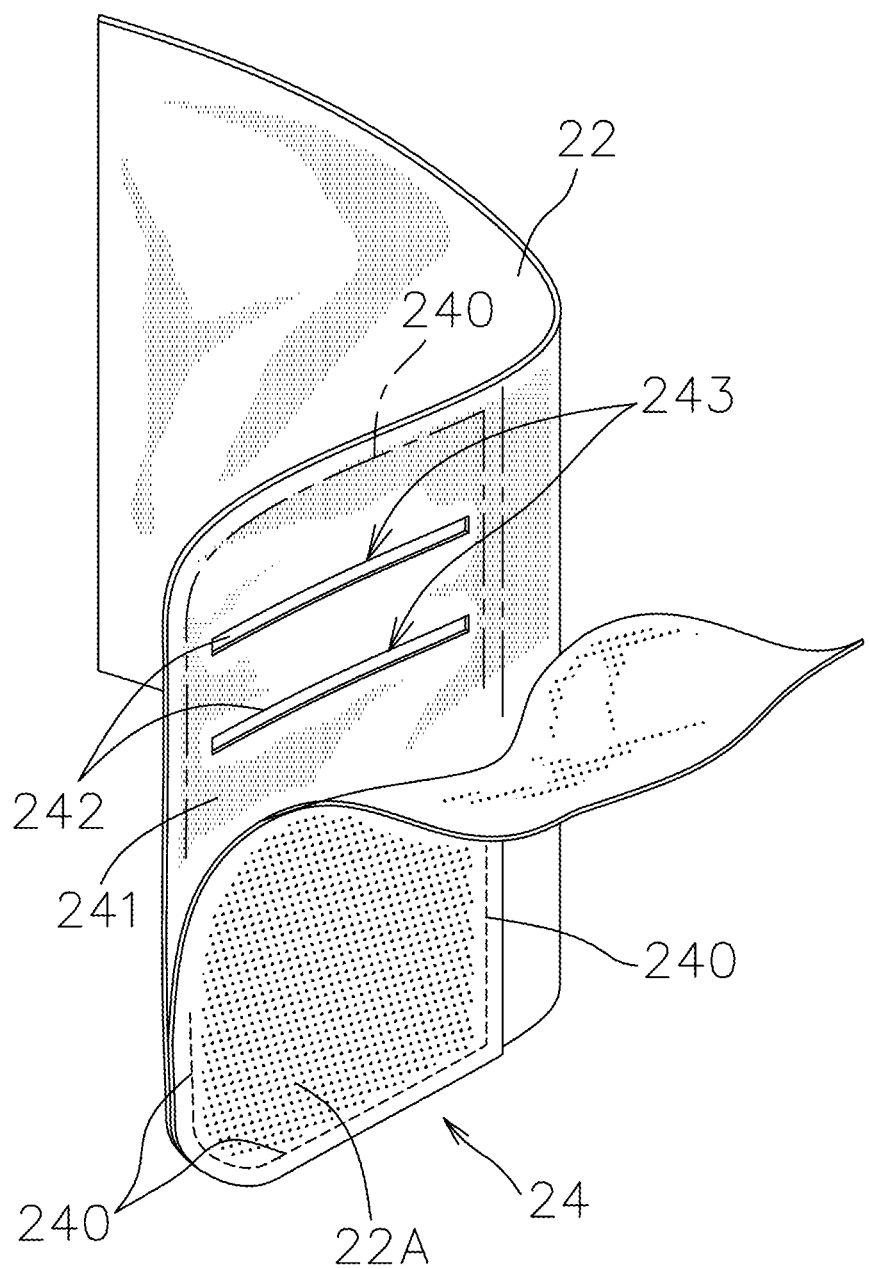
FIG. 7 is a schematic view of an absorbing and positioning device used during a healing period in accordance with an embodiment of the present invention.

With reference to FIGS. 6 and 7 for an application of a therapeutic bra structure during the repairing period after surgery healing in accordance with another embodiment of the present invention, the therapeutic bra structure further comprises an absorbing and positioning device 24 installed onto the elastic adjusting assembly 20 (wherein the absorbing and positioning device 24 is disposed on both of the elastic adjusting layers 21, 22 separately at the same time, and it is disposed on the elastic adjusting layer 22 in this embodiment). The absorbing and positioning device 24 comprises an outer positioning piece 22A installed on the elastic adjusting layer 22 and disposed in an area formed by extending the elastic adjusting layer 22 inwardly from an outer edge (wherein the outer positioning piece 22A is extended towards the inner side of the original end adhesive assembly 223 to an appropriate width in a preferred embodiment. In other words, an adhesive fastener (such as a VELCRO® tape) is formed on an outer surface of the outer positioning piece 22A. A positioning lining 241 is disposed on the inner lining relative to the outer positioning piece 22A and formed in an area formed and extending from the outer edge elastic adjusting layer 22. Therefore, the absorbing and positioning device 24 increases the width of the original end adhesive assembly 223 and is sewed on the elastic adjusting layer 22 to form its foundation assembly. Therefore, after the outer positioning piece 22A and the positioning lining 241 are fixed and combined at their peripheries (by a suture 240), so that a positioning strap space 243 is formed between the outer positioning piece 22A and the positioning lining 241. Now, the positioning strap space 243 forms a positioning pocket, and at least one opening 242 is formed at the positioning strap space 243 (or positioning pocket) on the positioning lining 241. In this embodiment as shown in the figure, two openings 242 are formed, and the positions of the openings 242 are not limited. For example, the opening 242 may be formed at an upper position, but not on the suture 240. In other words, the upper part is not sewed.

Figure 8:
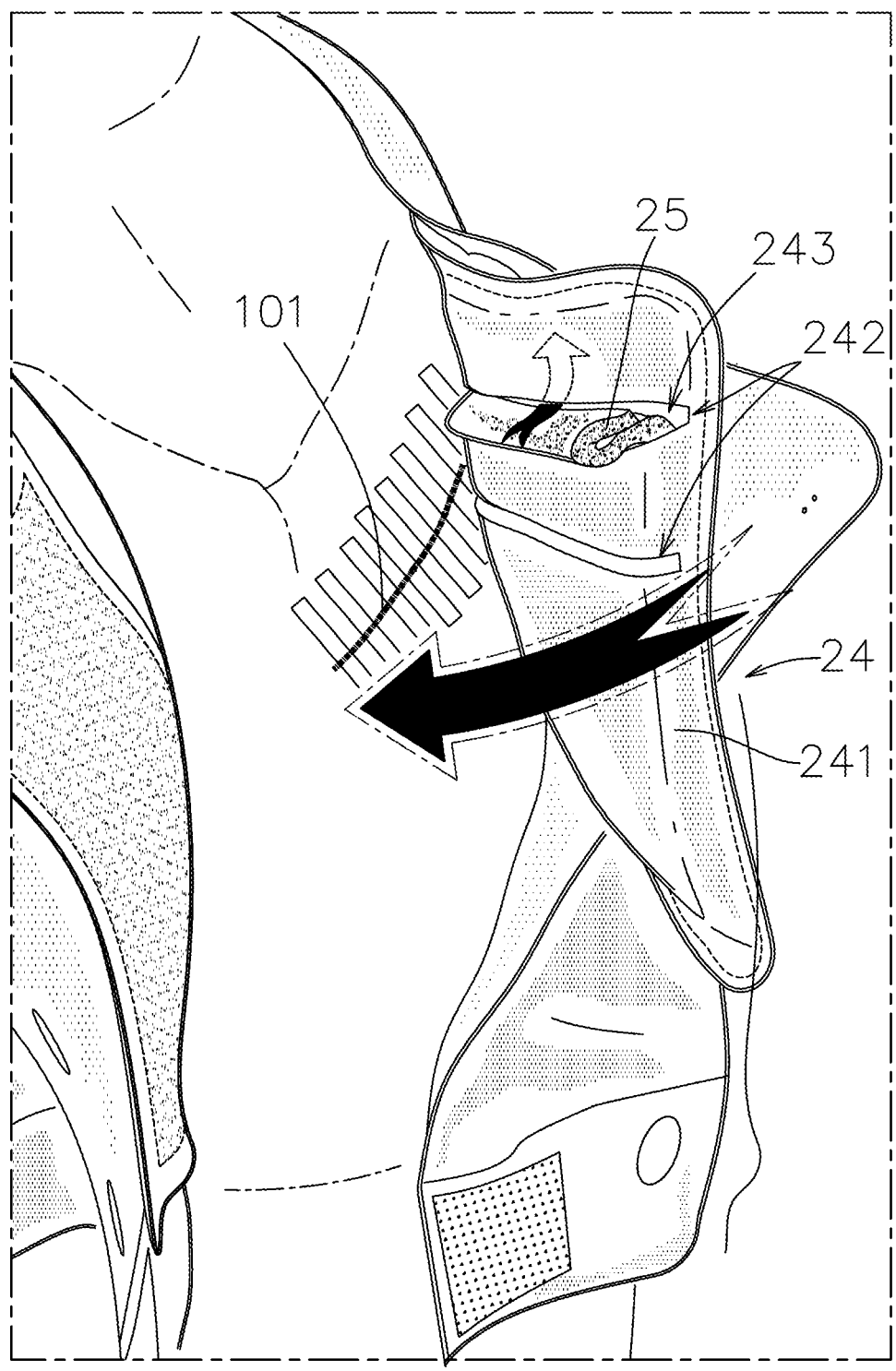
FIG. 8 is a first schematic view of an absorbing and positioning device used during a healing period in accordance with an embodiment of the present invention.
Figure 9:
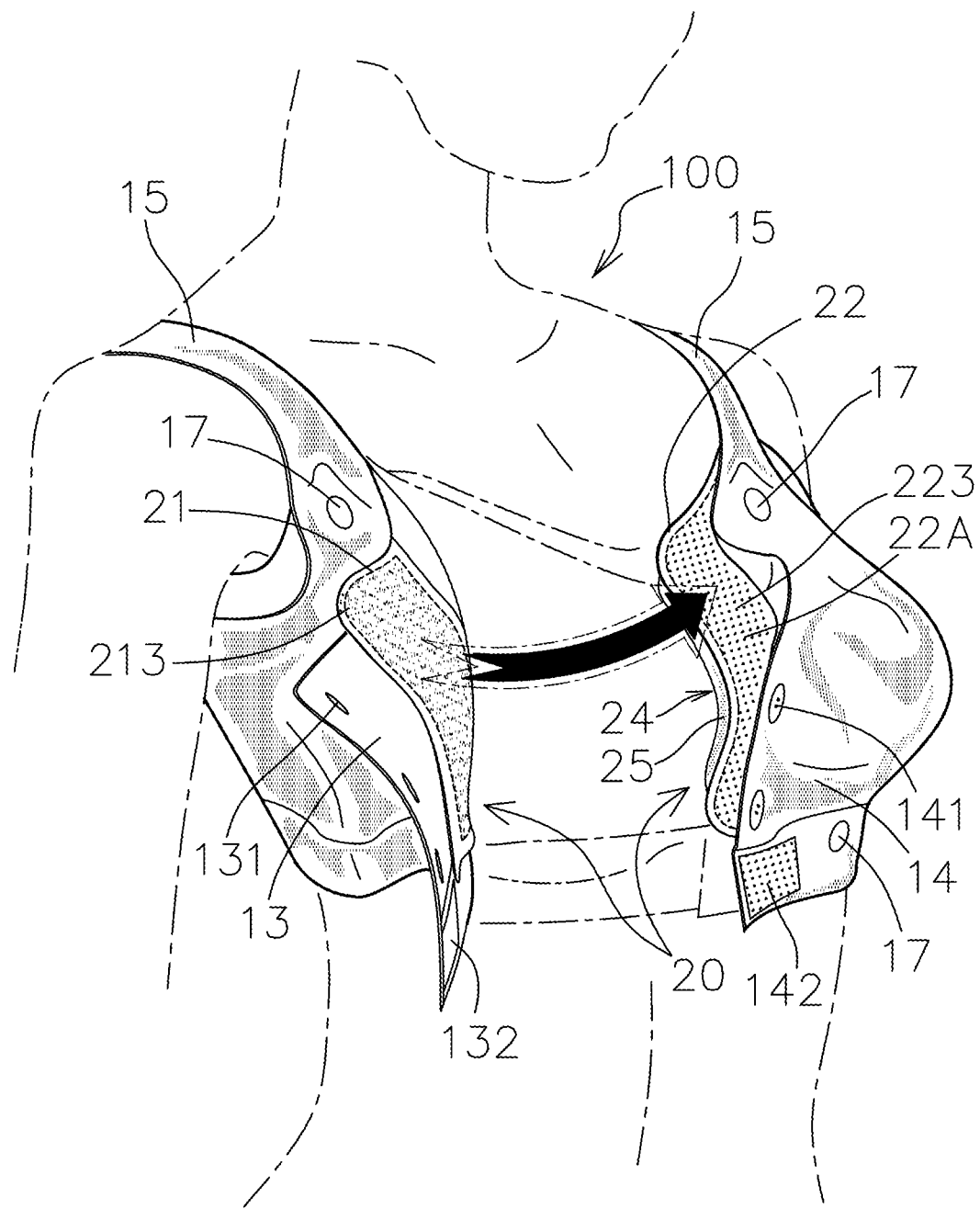
FIG. 9 is a second schematic view of an absorbing and positioning device used during a healing period in accordance with an embodiment of the present invention.

With reference to FIGS. 8 and 9 for the positioning strap space 243 used for installing an absorbing cotton strap 25, the absorbing cotton strap 25 is put into the positioning strap space 243 from the opening 242 and fixed, so that the absorbing cotton strap 25 is limited and positioned by the positioning lining 241. During the use of a bra with the therapeutic bra structure of the present invention, the absorbing cotton strap 25 is attached to the surgical wound to press the surgical wound appropriately and absorb the blood stasis at the surgical wound and prevent blood leakage, so as to avoid re-contaminating the wound or prevent the blood from penetrating through and staining the bra.

In a preferred embodiment, the absorbing cotton strap 25 has an appropriate length. When the absorbing cotton strap 25 is put into the positioning strap space 243 from the opening 242 and bent/folded towards the inner side (not shown in the figure, but the detailed description will be given below), the absorbing cotton strap 25 covers the positioning lining 241, so that the surgical wound is attached and covered by the absorbing cotton strap 25 directly, and the positioning lining 241 is separated by the absorbing cotton strap 25 to further improve usability.

Figures 10A, 10B:
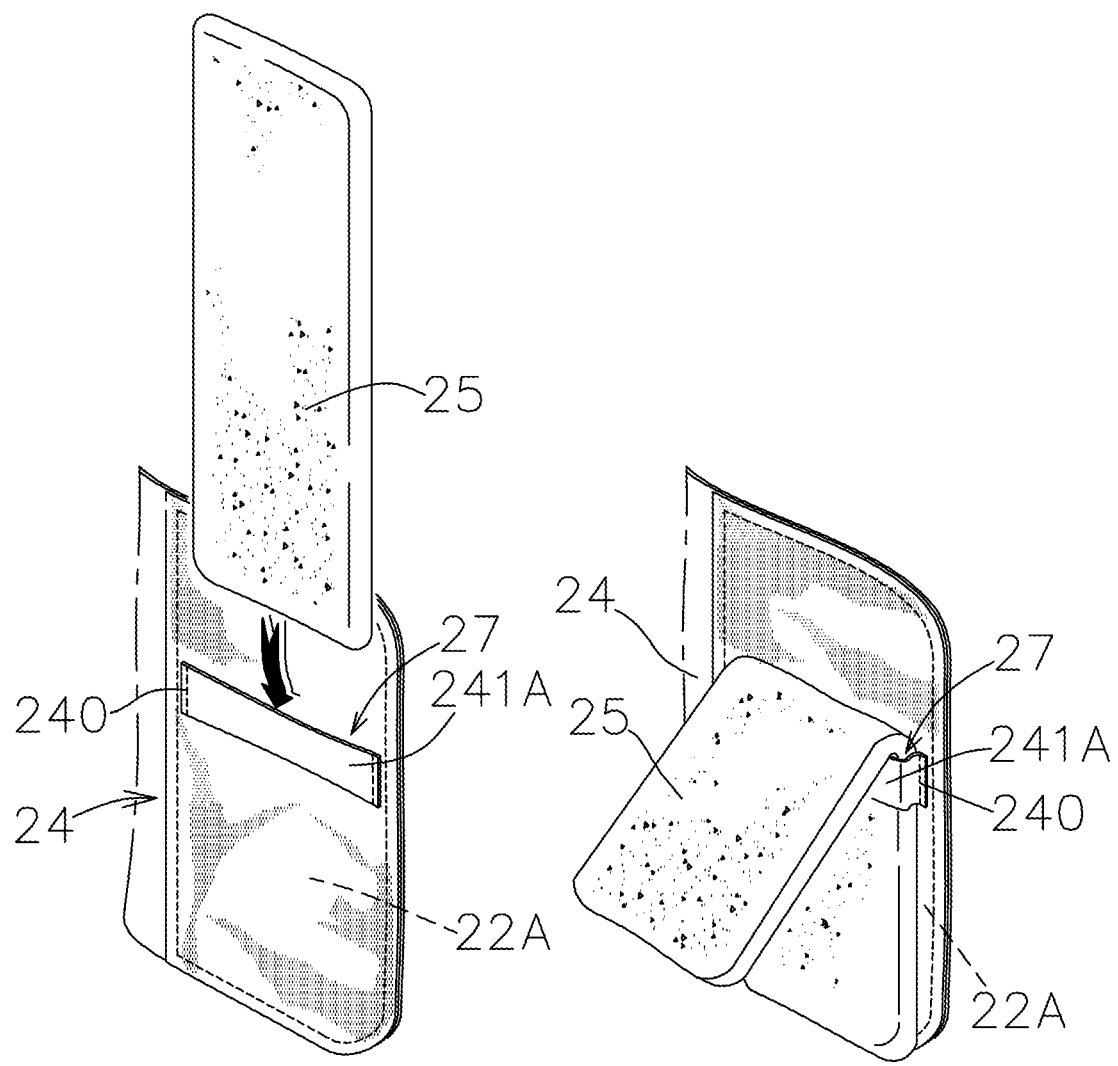
FIGS. 10A~10C are schematic views showing a change of an application during a healing period in accordance with an embodiment of the present invention.

With reference to FIG. 10A for an application of a therapeutic bra structure during a repairing period after surgery healing in accordance with the present invention, the difference resides on that the positioning lining 241A forms at least one strap that is fixed onto an inner side of the outer positioning piece 22A as shown in the figure, and distal sides of the positioning lining 241A are sewed and fixed onto the outer positioning piece 22A by the suture 240, and a positioning strap space 27 is formed between the positioning lining 241A and the outer positioning piece 22A and provided for passing and installing the absorbing cotton strap 25, so that the absorbing cotton strap 25 is restricted and positioned by the positioning lining 241A. Wherein, the quantity of the positioning lining 241A and the position of the positioning lining 241A relative to the outer positioning piece 22A are not limited and can be adjusted flexibly.

Figure 10C:
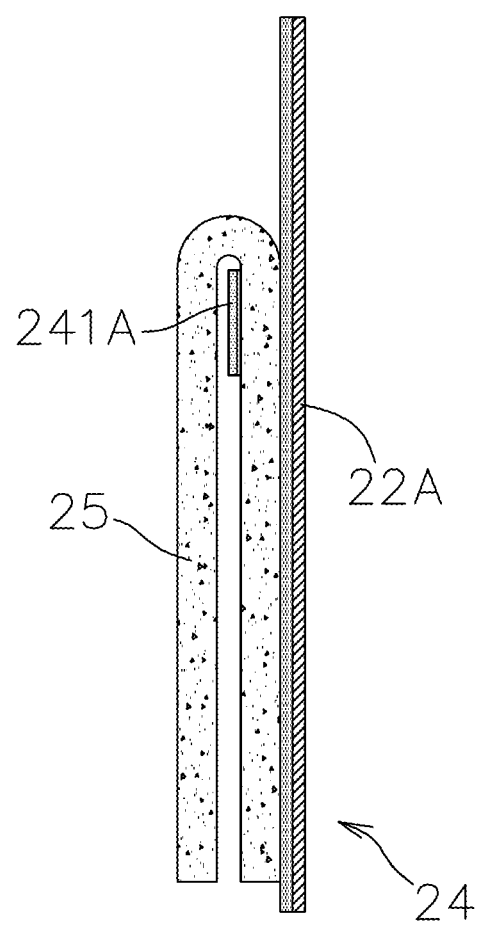

With reference to FIGS. 10B and 10C for an application of a therapeutic bra structure during a repairing period after surgery healing in accordance with an embodiment of the present invention, after the absorbing cotton strap 25 passes through the positioning strap space 27 of the positioning lining 241A, the absorbing cotton strap 25 with an appropriate length is ben or folded towards the inner side, so that the absorbing cotton strap 25 covers the positioning lining 241A, and the absorbing cotton strap 25 is attached directly with the surgical wound, and the positioning lining 241A is separated from the surgical wound. Therefore, the absorbing cotton strap 25 can be used to absorb the blood stasis and stop the blood leakage at the surgical wound to prevent blood from touching the positioning lining 241A or penetrating through and staining the bra.

In the aforementioned therapeutic bra structure of the present invention, this structure facilitate women to wear a therapeutic bra in a breast surgery healing period and allows users to adjust the elasticity and ensure the effects of healing the wound stably, facilitating the installation and use of the drainage tube and artificial blood vessel, and ensuring the safety of wearing bra after a female breast surgery. In addition, the present invention can cover and press the wound appropriately and squeeze or remove some blood stasis and prevent blood leakage and handle the blood stasis and blood leakage property, so as to avoid re-contaminating the wound or prevent blood from penetrating through and staining the corset that creates a visual psychological burden. During the use of the therapeutic bra structure in a breast repairing period after surgery healing, this invention can recover the patient's normal life quickly and prevent further psychological harm.

What is claimed is:

1. A therapeutic bra structure, comprising:
    a bra body, having a bra layered member, with a side bra layered member disposed on both sides of the bra layered members separately, and a fastener assembly or an adhesive assembly combined with an edge of the two side bra layered members;
    an elastic adjusting assembly, having two elastic adjusting layers, each having an elastic and permeable layered member, and the two elastic adjusting layers being combined and fixed to an inner side of the bra layered member and having an end adhesive assembly disposed on an outer side of the two elastic adjusting layers separately and provided for a purpose of combining and positioning to the bra layered member.

2. The therapeutic bra structure according to claim 1, wherein the bra layered member has two corresponding longitudinal strip shaped adhesive assemblies, and the elastic adjusting layer has a longitudinal strip shaped adhesive assembly disposed on an outer side of an inner edge of the elastic adjusting layer.

3. The therapeutic bra structure according to claim 1, wherein the bra layered member has two corresponding bumpy adhesive assemblies, and the elastic adjusting layer has a bumpy adhesive assembly disposed on an outer side of an upper edge of the elastic adjusting layer.

4. The therapeutic bra structure according to claim 1, wherein the bra layered member has two shoulder straps disposed thereon, and the shoulder strap has an adjusting fastener.

5. The therapeutic bra structure according to claim 1, wherein the bra layered member has two corresponding pockets, and each of the two pockets has an accommodating opening.

6. The therapeutic bra structure according to claim 1, wherein the bra layered member has at least one positioning hole provided for passing, installing, and positioning a drainage tube or a blood transfusion tubing an artificial blood vessel.

7. The therapeutic bra structure according to claim 5, further comprising at least one breast prosthesis pad, and the breast prosthesis pad further comprising a breast prosthesis pad member and a breast prosthesis strap, and the breast prosthesis strap being put into the pocket through the accommodating opening for the purpose of positioning to the breast prosthesis pad member and the breast prosthesis strap.

8. The therapeutic bra structure according to claim 1, wherein the elastic adjusting layer further comprises an absorbing and positioning device, and the absorbing and positioning device comprises an outer positioning piece and a positioning lining combined with each other.

9. The therapeutic bra structure according to claim 8, further comprising a positioning strap space defined between the outer positioning piece and the positioning lining, and a absorbing cotton strap being installed in the positioning strap space.

10. The therapeutic bra structure according to claim 9, wherein the positioning strap space is a positioning pocket, and the positioning pocket has at least one opening formed on the positioning lining.

11. The therapeutic bra structure according to claim 9, wherein the positioning lining is strip shaped, and both distal ends of the positioning lining are sewn and fixed to the outer positioning piece, and the positioning strap space is provided for passing, installing, and positioning the absorbing cotton strap.

12. The therapeutic bra structure according to claim 9, wherein the outer positioning piece is provided for forming the end adhesive assembly thereon.

13. The therapeutic bra structure according to claim 9, wherein the outer positioning piece is formed by the end adhesive assembly.

14. The therapeutic bra structure according to claim 9, wherein the absorbing cotton strap covers the positioning lining.

* * * * *